United States Patent [19]
Robinson

[11] Patent Number: 5,149,317
[45] Date of Patent: Sep. 22, 1992

[54] LIGHT-PULSING, VISUAL STIMULUS ENTERTAINMENT DEVICE AND METHOD

[75] Inventor: Wilbur A Robinson, Little Rock, Ark.

[73] Assignee: I Q International, Inc., Little Rock, Ark.

[21] Appl. No.: 419,950

[22] Filed: Oct. 11, 1989

[51] Int. Cl.⁵ ............................................. A61M 21/00
[52] U.S. Cl. ........................................ 600/27; 600/28
[58] Field of Search ........................... 600/26, 27, 28; 84/464 R

[56] References Cited

U.S. PATENT DOCUMENTS

| | | | |
|---|---|---|---|
| 4,172,406 | 10/1979 | Martinez | 84/464 R |
| 4,315,502 | 2/1982 | Gorges | 600/27 |
| 4,790,629 | 12/1988 | Rand | 350/321 |
| 4,809,584 | 3/1989 | Forrest | 84/464 R |
| 4,902,274 | 2/1990 | Gleeson, III | 600/27 |
| 4,928,568 | 5/1990 | Snavely | 84/464 R |

*Primary Examiner*—William E. Kamm
*Assistant Examiner*—Kevin Pontius
*Attorney, Agent, or Firm*—Ronald P. Kananen

[57] ABSTRACT

A device and method for stimulation of visual perception by a subject having his eyes closed, by illuminating the closed eyelids with light pulses, particularly in association with music or other sounds provided to his or her ears. Different light pulse sequences can be applied to the subject's two eyes, for instance simultaneously with the two channels of stereo sound supplied to the subject's ears. The device is provided so that the sound signal modulates the visual signal, such as the widths and separations of the light pulses in the light pulse sequences illuminating the subject's eyes, in a manner to which the subject's senses are particularly responsive. With such stimulation of the senses, the subject can perceive or observe, with closed eyes, a large variety of patterns and colors in his visual field. The patterns and colors occur and change on a variety of time and space scales, in some correspondence with the sound, but with some non-reproducible or chaotic characteristics as well. The effect provides entertainment and relaxation, and allows exploring the interplay in the brain of the light and sound senses.

12 Claims, 4 Drawing Sheets

LIGHT-PULSING, VISUAL STIMULUS ENTERTAINMENT DEVICE AND METHOD

BACKGROUND OF THE INVENTION

The invention relates to the visual perceptions by a human subject exposed to light pulses of varying time duration and separation, particularly in conjunction with sound which is supplied to the subject's ears and also used to modulate the light pulses.

Much remains to be explored and learned about the faculties of sight and sound and the associated workings of the brain. Various forms of entertainment and relaxation, almost too numerous to mention, arise from pastimes employing these senses. Thus, slightly different stereo images supplied to the two eyes of a subject can simulate depth of field, in the perceptions of the subject. Similarly yet not entirely the same, stereo music can provide its own sensation of geometrical location with respect to each source of sound in audio stereo.

Various devices have been developed in recent years for use in both stimulating and patterning brain functions in the fields of entertainment, psychology and learning. The brain utilizes wave patterns in order to function, and it is known that light and sound stimuli can affect brain wave patterns and actually alter the flow of these brain wave patterns.

Music signals have been used in "light organ" devices to modulate the intensity and flicker rate of multicolor lights, frequently with different frequency bands controlling different colored lights. Usually, the light output of these devices increases with intensity of the sound. In some cases reflecting foil has been used to scatter more than one color light at a time.

Another type of prior art is described in U.S. Pat. No. 4,315,502, involving a device for stimulation or relaxation. Respective pulses of light are applied to both eyes and of sound to both ears, in alternating or simultaneous fashion, to cause an interplay between the front, rear, right and left parts of the brain. Light is stated to stimulate the rear of the brain, and sound to stimulate the front of the brain. Brightness (that is, intensity) of the lights is set by a variable duty oscillator, and a square pulse of variable selectable frequency is provided to a phase control to alternate or synchronize the left vis a vis the right of both the audio and light signals, and the audio vis a vis the light signals. A "tock" sound generator is synchronized with the square wave, for instance to deliver successive tock sounds to alternating ears of the human subject.

This prior art does not involve the combining of two sequences of pulses for determining the light pulses provided to the subject. This prior art further does not involve the sequences of pulses for the light signal being the result of modulation of an initial pulse sequence by a pulse sequence corresponding to an audio signal, wherein the audio signal is provided to be heard by the subject simultaneously with the modulated light signal. This prior art has not involved the visual stimulation of the subject's closed eyes in the manner of the present invention, thus without the brain being distracted by the processing of a visual image.

SUMMARY OF THE INVENTION

It is an object of the present invention to carry forward these limited efforts of the prior art, particularly into the realm of stimulating perceptions by the brain of structures, patterns and colors with time and space variations, as a result of modulations of a base or reference pulse train with a further pulse train.

It is a further object of the invention to stimulate the perception by the brain, in all ways that this can be realized using the senses of sight and sound, of coincidences between the modulated sequence of light pulses and the audio signal from which the modulating pulse sequence is formed, involving more than a mere flickering dependent on sound intensity.

It is a further object of the invention to provide in the modulation chaotic, random or otherwise non-repetitive effects, while maintaining recognizable correlations between the light pulses provided to the two eyes and the modulating signals.

It is a further object to provide a synergism of perception from the exercise of the sound and sight senses, since for the case of the modulating signal being audio signals which are also supplied to the ears of the subject, these varying but discernable correlations can have dramatic effect in the perceptions and mind of the subject.

It is a further object of the invention to provide as chaotic a visual stimulus as possible, for entertainment or other visual stimulus purposes, while still reflecting in the visual stimulus the rhythm in an audio sound simultaneously provided to a user.

The present invention relates to the art of learning and relaxation aids, and more particularly to a device and method which releases psychological and physiological stress and tension primarily by stimulating the senses of hearing and sight. The present invention also allows the enjoyable exploration of the interplay of these senses in the cognitive consciousness of the brain.

DETAILED DESCRIPTION OF PREFERRED EMBODIMENTS

Figure 1:
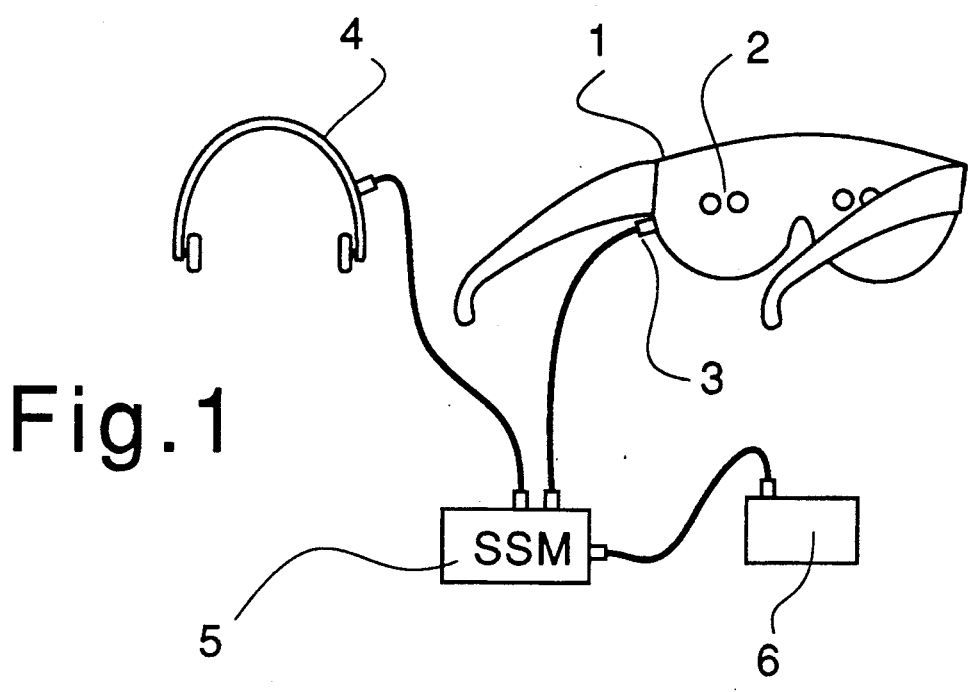
FIG. 1 shows an embodiment of the invention, wherein the light sources are mounted on the inside of a pair of dark glasses and are plugged in along with earphones to the stimulus module, which in turn is plugged into a radio or compact disk player.

The following references to the drawings are for the purposes of illustrating a preferred embodiment of the invention only, and should not be construed as limiting its scope. FIG. 1 indicates how a pair of dark glasses 1 can be fitted to support two pairs of light-emitting diodes LEDs 2 on the interior side opposite the eyes of a person. Each LED pair 2 separately illuminates a respective closed eyelid of the person. The LED circuitry on the glasses (supplied by wires 3) and the earphones 4 for an audio signal are plugged into an stimulus signal module SSM 5. The SSM 5 is plugged into the audio outlet of a radio, compact disk player or other source 6 of an audio or other signal to be used as a signal to modulate the light signal. For portability, batteries can be provided in the SSM 5 for driving the LEDs 2.

Figure 2:
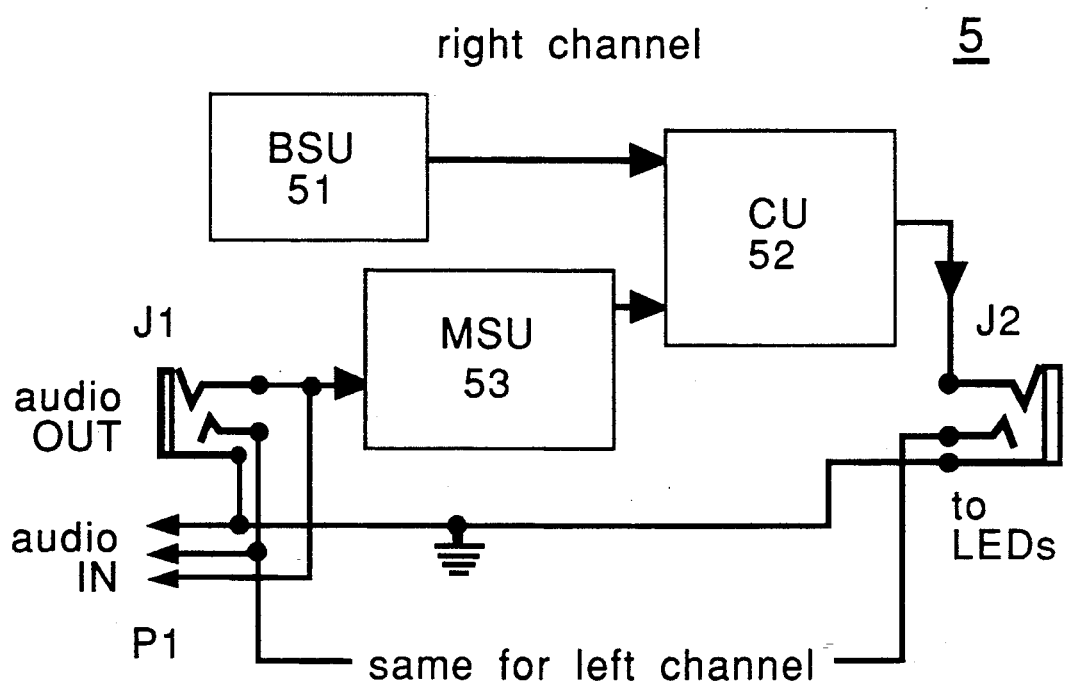
FIG. 2 shows an embodiment of the stimulus signal module, wherein each of the left and right channels has base signal, modulating signal and combining units.

The embodiment of the stimulus module SSM 6 shown in FIG. 2 includes a ⅛ inch diameter stereo phone plug P1 which is attached to the end of a 15 inch pigtail (not shown). This plug P1 is inserted into the headphone jack of a music source 6 (radio, tape, CD, etc.). A ⅛ inch diameter stereo phone jack J1 of the same type as found on the music source 6 receives the plug attached to the headphone supplied with the music source. The volume of the music is set by the control on the music source. The ⅛ inch phone jack J2 receives the ⅛ inch diameter phone plug P2 (FIG. 3d) for the wires supplying the signal and power to the LEDs 2 on the glasses 1.

It is to be noted that a right channel and a left channel for both the music and the light signal are shown for this embodiment, although in some variations of the invention only a single audio or light signal channel might be employed. The right and left channel circuitry is generally identical, as indicated. Certain items are shared by both channels, such as the connectors and the battery pack. The following description pertains to the right channel for reference, but applies equally for the left channel.

In the stimulus signal module SSM 5, the base signal unit BSU 51 produces a base or reference pulse sequence which is provided as a first input to a combining unit CU 52. The audio signal is fed into the modulation signal unit MSU 53, in which a modulating signal is generated and output as a respective pulse sequence. This output from the MSU 53 is provided as a second input into the combining unit CU 52. The audio signal is also provided to the audio OUT jack J1, for the earphones. In the combining unit CU 52 the base signal pulse sequences are modulated by the pulse sequence of the modulating signal, and a corresponding modulated pulse sequence is output via jack J2 and wires 3 (FIG. 1), for the light source circuitry on the glasses shown in FIG. 3d.

Figure 3A:
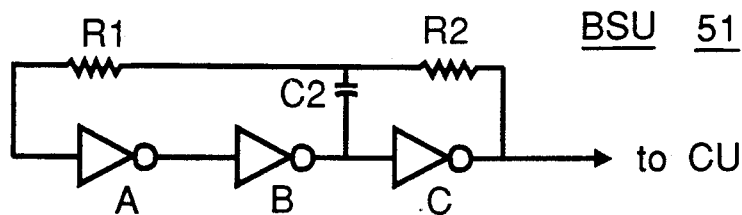
FIGS. 3a, 3b and 3c show embodiments of the base signal, modulating signal and combining units, the latter two each utilizing an EXCLUSIVE OR logic gate.
Figure 3B:
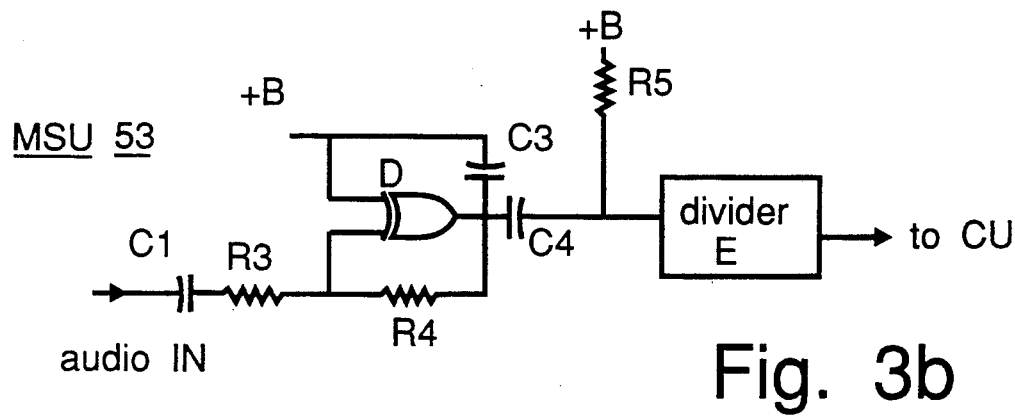
Figures 3C, 3D:
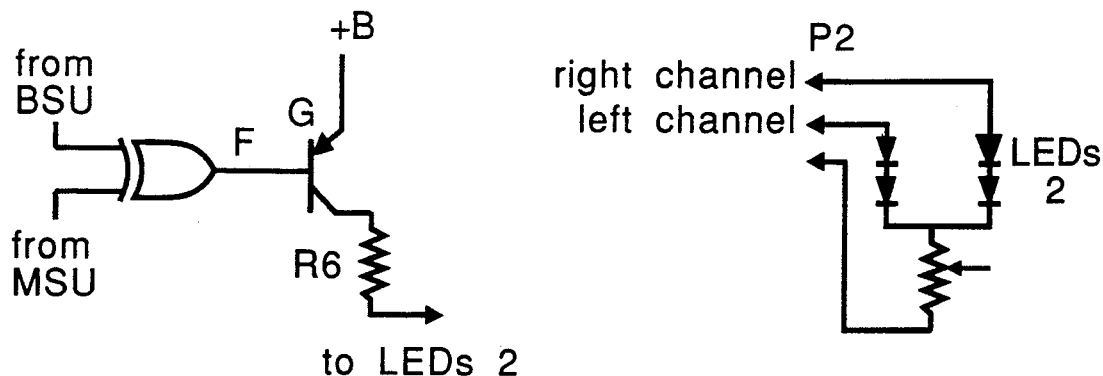
FIG. 3d shows the circuit with the light sources for mounting inside the glasses.

For the embodiments of the units of the stimulus signal module SSM 5 illustrated in FIGS. 3a to 3c, if the music source is turned off, disconnected, the volume turned down, or if no music is produced for any other reason, the blink rate of the eye stimulus module is determined by the output of the base signal unit BSU 51 of the channel. The basic signal unit BSU 51 as shown in FIG. 3a is an astable multivibrator formed by the inverting IC gates A, B and C and the resistors R1 (10M ohm nominal) and R2 (1M nom.) and the capacitor C2 (100nF nom.). These components are selected so that the multivibrator has a natural frequency of oscillation of roughly 4 Hz.

All of these components of the BSU 51 (and C1, C4, R3, R4, R5 below for respective reasons) are preferably selected from the type having large tolerances in the (that is, not very precise) values for their respective characteristic, or from the types having large variation with temperature, since this leads to a desirable variation in the rate of the pulses in the base signal. This can also provide variations in the duty cycle of the high/low levels in the pulse sequence of the base signal. Thus the pulse rate may be somewhere in the range for instance of 3 to 5 Hz, or even 2 to 6 Hz in direct sunlight. The duty cycle is nominally 50%, but can vary for instance between 40 to 60%. Thus variations arise between the two channels of a device, and between different devices. These random variations can add to the effects sought by their use.

Gates A and B are series-connected to produce a non-inverting logic level buffer, and gate C provides logic inversion. When power is first applied, the input of gate A may be either at logic level 0 (0 volts) or at logic level 1 (+B). If it is assumed that the initial state of the input of gate A to be 0, then the output must be logic level 1 by definition. The output of gate B will then be logic level 0. The 0 on the input of gate C causes a logic level 1 on the output of C. This high level will cause C2 to begin charging through R2. When the voltage on C2 reaches the threshold level of gate A for the high logic level, it will switch, causing the input of gate C to become a 0. This action is repeated approximately 8 times each second. This cycle will be repeated for so long as power is applied. The converse of this action would occur if the initial state were a 1 instead of a 0, and in any event will continue for so long as power is applied.

Even though gate D is nominally a logic device, any CMOS inverter can be used as a linear amplifier if an appropriate bias is applied. Gate D, which is an EXCLUSIVE OR, has been configured as an inverter by connecting one input to the logic 1 level. The resulting inverter is biased by the 10M resistor R4. A dc feedback component from the output to the other input of gate E causes a quiescent operating point of approximately B/2 to be established. This operating point can and will depart from the ideal B/2 level because of process variations that slightly modify the transfer characteristics of the gate. The only effect of this departure will be a slight asymmetry of amplification, that is, the positive and negative swing of the amplifier will not be equal.

As seen for the modulating signal unit MSU 53 of FIG. 3b, the audio from the music source is applied to an amplifier composed of gate D and resistors R3 (47K) and R4 (10M). A coupling capacitor C1 (100 nF nom.) is for isolating the different DC levels present at the music source output and the amplifier input.

The gain of the amplifier is set by the ratio of R4/R3 to a high value, for instance 200 (46 db) as approximately occurs for the above embodiment. This means that an input of +B/200, or approximately 0.02 V (peak to peak) is sufficient to cause full output. Any additional input level will cause the amplifier to become saturated. The capacitor C1 allows the continuously changing audio from the music source to be coupled to the amplifier. The output of the amplifier is $$V_{out} = -V_{in} * R4/R3$$

Whenever the magnitude of this output is greater than B/2, the amplifier ceases to be a linear device and produces a "clipped" version of the input.

This high level of amplification is used to convert the analog music signal to a quasi-digital signal, with frequency components that are directly related to the frequency components of the audio signal. Thus, as soon as the audio signal falls below the above-mentioned threshold of 0.02 V, the output of gate D returns to a quiescent level of B/2. Since this threshold is generally a very small part of the amplitude of any audio signal, a pulse train with effectively vertically rising and falling edges is provided. The width of each pulse depends on the particular overlap of frequencies and their phase at each instant along each pulse. Great variations in pulse width can arise, where many audio frequencies overlap to produce a low or high envelope of the instantaneous field. On the other hand, a single audio frequency will produce a pulse train of great regularity.

The capacitor C3 (10 nF) connected to the output of gate D is to reduce the tendency of the amplifier to oscillate at high frequencies.

Elements C4 (100 nF nom.) and R5 (10K nom.) provide DC restoration so that the resting state of the input of pulse-count divider E is at a known level (+B). Divider E can be provided as an 8-stage binary counter (Motorola 14520) to reduce the frequency of the quasi-digital conditioned music signal by a factor of 256. This counter would for instance output a high level for the first 128 pulses, and a low level for the next 128 pulses. Thus a musical note with a frequency of 2560 Hz would produce an output of 10 Hz, and that the middle C note at 256 Hz would produce a frequency of 1 Hz.

As shown for the combining unit CU52 in FIG. 3c, gate F provides the logic EXCLUSIVE OR function. Transistor G (2N3906, or any other general purpose PNP) and resistor R6 provide a voltage-to-current translation. This current is used to control the light-emitting diodes in the stimulus signal module.

Figure 4:
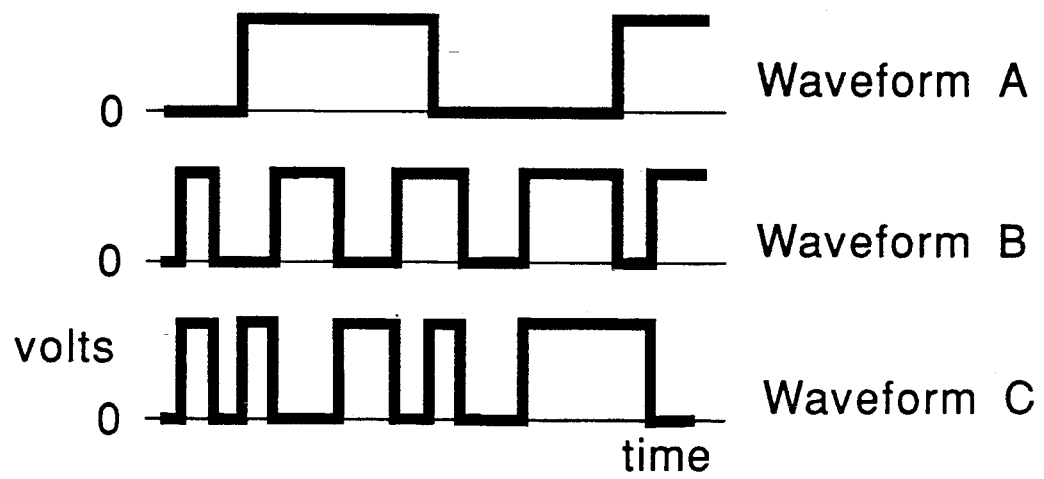
FIG. 4 shows example waveforms for the pulse sequences of the combining unit, namely the base and modulating signal inputs and the resulting output for driving one channel of the light signal.

As seen with the pulse sequences in FIG. 4, this gate combines the base signal output of gate C of the astable multivibrator (waveform A) and the modulation signal output of the divider E (middle waveform) in such a way that the conditioned music signal modulates the ON/OFF pattern of the astable multivibrator, producing a modulated light pattern with pseudo-random pulse widths (waveform C). The phases and the pulse widths of the two inputs are independent, and when one rises or falls while the other is at high or low state, the result is a chopping of the steady one into a shorter pulse which appears in the output pulse sequence to the LEDs. This can be seen for both the rising and falling of the first pulse in waveform A (the input from the BSU), each of which chops a corresponding flat part of the second input (of waveform B from the MSU) and produce a corresponding narrower-width pulse in the output (waveform C). On the other hand, on occasion the two inputs will have coinciding vertical edges (rising or falling at the same time), and this relatively more rare occurrence can act to produce a pulse in the output of width greater than in either input. This can be seen for the rising of the second pulse in waveform A, in which the width of the output pulse is greater than the corresponding pulse in waveform B. Depending on the separation of the pulses in waveform B, an output pulse of width greater than the pulses in waveform A is also possible.

Thus, dramatic changes in the output pulse can occur, depending on the modulating signal from the MSU53, and the random interaction of the two input signals in the combining unit CU52. Since the modulating signal from the MSU53 arises from the audio signal, striking correlations between what is heard and what is seen are both expected and indeed observed. Such correlations, with the superposed randomness inherent in the generation of the signals, would arise as well with single channel devices, and as well with a single BSU51 providing the same first input to both CUs. However, the effect is particularly interesting with full dual channels, as for the embodiment above with stereo audio channels.

It is to be noted that a symmetry obtains with respect to which is to be considered the modulating input and which is the input to be modulated, at least with the particular circuitry of the drawings as described above. Thus when either is at high level, gate F acts as an inverter with respect to the other input. Also, whereas the pulses of the second input (from the MSU53) are shown in FIG. 4 to be shorter, the opposite also can and would arise under normal conditions. This further demonstrates the symmetry of the terminology, namely that either could be considered to be the "modulating" input pulse sequence acting on the other input pulse sequence to produce the output pulse sequence for the light pulses, at least in the above embodiment of the present invention.

The nominal rate of 4 Hz for the pulses from the base signal unit BSU51 is selected to be more or less in the middle of an effective range for visual effects. Thus, different parts of the eye can perceive different maximum rates of flickering. While the periphery can sometimes detect flickering up to over 100 Hz, much of the eye can detect a much smaller maximum flicker rate, say roughly 40 Hz. The low end of the range of flicker rate of interest for visual effects can be set arbitrarily, say no lower than 0.4 Hz, corresponding to a change every 2.5 seconds.

The reason for selecting the divider E of FIG. 3b to divide the quasi-digitized audio signal by 256, aside from this number arising as two raised to the eight power, can now be seen. While a young girl can often hear a frequency as high as 20,000 Hz, the more common upper frequency limit audible to a typical adult's ear is maybe 7,000 Hz. The typical lower limit for a high quality audio system is 20 Hz, and roughly 100 Hz for the more common systems. Such two common audible limits can thus correspond closely to the above-mentioned flicker limits of 40 and 0.4 Hz. Thus, in a logarithmic sense, the frequency range of the output of the MSU can be considered to be roughly centered on the above 4 Hz frequency of the output of the BSU.

The use of LEDs2 emitting red light is of interest in the present invention, since it is the red part of the visible spectrum which is most capable of being transmitted through the flesh of the eyelids. Thus, illumination of red light onto a person's closed eyelids can evoke the sensation of seeing (with closed eyes) white light. But the pulsations generally evoke the sensation of seeing many different colors, in many continually changing patterns and combinations. There are thus many ways to be expected to produce these dynamic visual impulses, preferably in the mid-range of the human perception of these effects, or in any other part of the range where the perceiving power is strong. In other words, the object is to find the greatest coupling of these random yet correlated audio and visual signals with the cerebral mechanics of the audio and visual senses, both of which are mediated by the intermittent firing of the neurons connecting the eyes and ears to the brain. Clearly, comprehension of all these effects will remain a murky goal, involving efforts to categorize the nature of dynamic steady states conditions, variances therefrom, etc.

While the invention has been described in the more limited aspects of a preferred embodiment thereof, other embodiments of the invention have been suggested and still others will occur to those skilled in the art upon a reading and understanding of the foregoing specification. It is intended that all such embodiments be included within the scope of the invention as limited only by the appended claims.

We claim:

1. A visual stimulus device comprising
   a first circuit means for generating a first electrical signal comprising a sequence of pulses,
   a second circuit means for generating or otherwise providing, at least part of the time, a second electrical signal comprising a sequence of pulses,
   a combining circuit means for receiving at a first input said first electrical signal and at a second input said second electrical signal, and for outputting at an output an output electrical signal comprising a sequence of pulses corresponding to a respective combination of said first and second electrical signals, and
   illumination means for receiving said output electrical signal and providing a visual signal to a subject, said visual signal comprising a sequence of light pulses that is the same as said sequence of pulses of said output electrical signal,
   wherein said pulse sequence of said output electrical signal is in a frequency range which allows the subject to perceive the flashing of said visual signal,
   wherein said first circuit means comprises an astable multivibrator for generating said pulse sequence output therefrom at a respective frequency, and wherein further:
   said second circuit means comprises conversion means for receiving an audio signal as an input, and for converting said audio signal to said sequence of pulses of said output therefrom; and
   said combining circuit means comprises an exclusive OR gate, said exclusive OR gate having as first and second inputs two signals respectively corresponding to said sequences of pulses of said first and second electrical signals and an output corresponding to said sequence of pulses output from said combining means.

2. The device of claim 1, comprising said first circuit means including means for providing said frequency of said pulses of said pulse sequence output therefrom to be in the approximate range of 2 to 6 Hz.

3. The device of claim 1, said second circuit means further comprising:
   nulling means for selectively providing at least a part of the time that said second electrical signal is a null signal, instead of said sequence of pulses, wherein said output electrical signal output from said combining circuit corresponds to said electrical signal from said first circuit means when said second electrical signal from said second circuit means is said null signal.

4. The device of claim 1, wherein said second circuit means is such that the pulses of said sequence of pulses output from said second circuit means are approximately in a frequency range having an upper limit of at least a factor of ten greater than, and a lower limit of one tenth or less of, said frequency of said pulses of said pulse sequence output from said first circuit means.

5. The device of claim 1, said conversion means of said second circuit means comprising
   an exclusive OR gate which receives said audio signal at a first input and produces as an output a quasi-digital signal with pulses corresponding to said audio signal, and
   a frequency divider operatively connected to receive said output from said exclusive OR gate of said conversion means, said frequency divider providing as an output said second pulse sequence input from said second circuit means to said combining circuit means.

6. The device of claim 5, said frequency divider comprising means for providing said second pulse sequence as said output to said combining circuit means with a dividing factor on the order of 250, said dividing factor being with respect to said pulses of said quasi-digital signal.

7. The device of claim 5, said combining circuit comprising an exclusive OR gate having as first and second inputs signals respectively corresponding to said sequences of pulses of said first and second electrical signals and an output corresponding to said sequence of pulses output from said combining means.

8. The device of claim 1, wherein
   said first and second circuit means include means for providing that the range of frequency of said second electrical signal generated from said second circuit means is centered on the frequency of said first electrical signal generated from said first circuit means.

9. The device of claim 1, said astable multivibrator comprising first, second and third inverters respectively connected successively in series in the downstream direction, two resistors connected in series between the input of first inverter and the output of the third inverter, and a capacitor connected at one terminal between the second and third of said three inverters and at the other terminal between said two resistors.

10. A visual stimulus device comprising
    a first circuit means for generating a first electrical signal comprising a sequence of pulses,
    a second circuit means for generating or otherwise providing, at least part of the time, a second electrical signal comprising a sequence of pulses,
    a combining circuit means for receiving at a first input said first electrical signal and at a second input said second electrical signal, and for outputting at an output an output electrical signal comprising a sequence of pulses corresponding to a respective combination of said first and second electrical signals, and
    illumination means for receiving said output electrical signal and providing a visual signal to a subject, said visual signal comprising a sequence of light pulses that is the same as said sequence of pulses of said output electrical signal,
    wherein said pulse sequence of said output electrical signal is in a frequency range which allows the subject to perceive the flashing of said visual signal, and
    wherein said second circuit means comprises:
    an exclusive OR gate which receives an audio signal at a first input and which is biased as a linear device to produce therefrom a quasi-digital signal with pulses corresponding to said audio signal; and
    a frequency divider operatively connected to receive as an input a signal corresponding to said quasi-digital signal, said frequency divider providing as an output said sequence of pulses output from said second circuit means to said combining circuit.

11. A device for stimulating visual perceptions by a human subject having his or her eyes closed, by illuminating separately the left and right eyelids of the subject in synchronism with stereo sound supplied to the left and right ears of the subject, said device comprising
    left and right eye illumination means, for providing separate sequences of light pulses to the left and right eyes of the subject, in response to two respective electrical pulse sequences input to said eye illumination means, at least one reference pulse means for generating at least one pulse sequence of at least one frequency in the range of interest for said visual perception to be stimulated, and a pair of modulation means for modulating each said at least one pulse sequence from said at least one reference pulse means, to provide a respective pair of modulated pulse sequences which are provided to said illumination means as said two electrical pulse sequences, each said modulation being determined by factors including the frequency and phase of the respective reference pulse sequence and the respective audio signals of said stereo sounds, wherein each said modulation effects the separation and width of the pulses of light reaching the eyelids of the subject, including by introduction of a chaotic variation, and wherein each said modulation means includes a respective frequency multiplier, each said frequency multiplier comprising an exclusive OR gate.

12. A method of stimulating visual perception by a subject listening to music and having pulses of light falling on his closed eyelids, said method comprising generating first and second sequences of pulses, said first sequence of pulses being independent of said second sequence of pulses, wherein said first sequence of pulses is determined at least in part but not entirely by audio signals corresponding to said music, combining by means of an exclusive OR gate said first and second pulse sequences in a predetermined manner dependent on the width and relative phases of the pulses to produce a corresponding output pulse sequence, the logic level of said output pulse sequence depending at any time on the logic levels of said first and second sequences of pulses corresponding to the same time, and providing said pulses of light according to said output pulse sequence.

* * * * *